(12) United States Patent
Venbrux et al.

(10) Patent No.: US 7,914,493 B2
(45) Date of Patent: Mar. 29, 2011

(54) WIRE GUIDE WITH ENGAGING PORTION

(75) Inventors: Anthony C. Venbrux, Round Hill, VA (US); Daniel J. Sirota, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 332 days.

(21) Appl. No.: 11/607,303

(22) Filed: Nov. 30, 2006

(65) Prior Publication Data

US 2007/0191778 A1    Aug. 16, 2007

Related U.S. Application Data

(60) Provisional application No. 60/741,626, filed on Dec. 2, 2005, provisional application No. 60/790,117, filed on Apr. 7, 2006.

(51) Int. Cl.
*A61M 5/178* (2006.01)
*A61M 25/00* (2006.01)

(52) U.S. Cl. .................. 604/164.13; 604/528; 600/585

(58) Field of Classification Search ................ 600/585; 604/164.13, 528, 20
See application file for complete search history.

(56) References Cited

U.S. PATENT DOCUMENTS

| | | | |
|---|---|---|---|
| 4,548,206 A * | 10/1985 | Osborne | 600/585 |
| 4,554,929 A | 11/1985 | Samson et al. | |
| 4,971,490 A | 11/1990 | Hawkins | |
| RE33,911 E | 5/1992 | Samson et al. | |
| 5,405,376 A * | 4/1995 | Mulier et al. | 607/127 |
| 5,728,198 A | 3/1998 | Leschinsky et al. | |
| 5,853,421 A | 12/1998 | Leschinsky et al. | |
| 5,871,501 A | 2/1999 | Leschinsky et al. | |
| 6,482,216 B1 | 11/2002 | Hiblar et al. | |
| 2002/0120238 A1* | 8/2002 | McGuckin et al. | 604/187 |

* cited by examiner

*Primary Examiner* — Nicholas D Lucchesi
*Assistant Examiner* — Rebecca E Eisenberg
(74) *Attorney, Agent, or Firm* — Brinks Hofer Gilson & Lione (57) ABSTRACT

A wire guide and a method for its percutaneous guidance within a body vessel are provided. The wire guide includes an outer component for insertion into the body vessel and a core wire disposed in the outer component and movable between first and second positions. The core wire includes an engaging portion that extends from the outer component to engage the body vessel when the core wire is in the second position.

10 Claims, 9 Drawing Sheets

WIRE GUIDE WITH ENGAGING PORTION

CROSS-REFERENCE TO RELATED APPLICATION

This patent application claims the benefit under 35 U.S.C. §119(e) of U.S. provisional patent application Ser. No. 60/741,626, filed Dec. 2, 2005 and entitled WIRE GUIDE WITH EXTENDABLE CORE WIRE, and of U.S. provisional patent application Ser. No. 60/790,117, filed Apr. 7, 2006 and entitled WIRE GUIDE WITH ENGAGING PORTION, the entire contents of each of which is incorporated herein by reference.

BACKGROUND OF THE INVENTION

1. Field of the Invention

This invention relates to wire guides used in diagnostic and interventional medical procedures. More specifically, this invention relates to wire guides used for access to complex distal anatomy for diagnostic and interventional procedures.

2. Related Technology

Figure 18A:
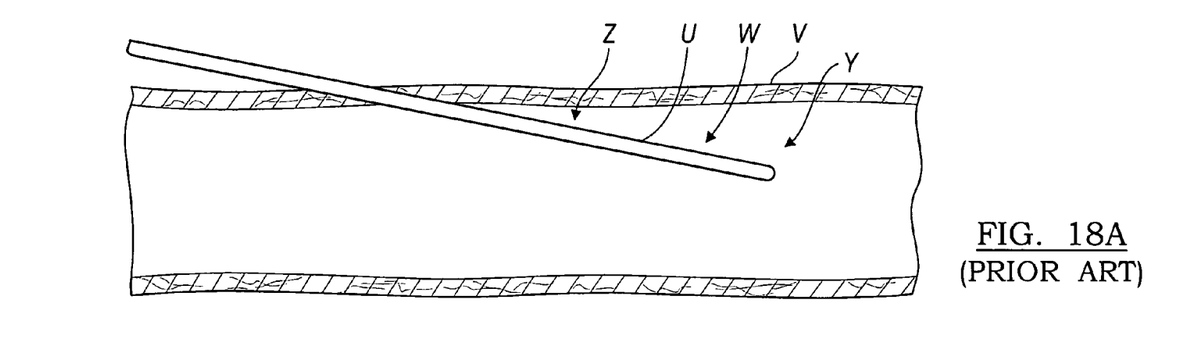
FIG. 18a is an environmental view of a wire guide known in the prior art being inserted into a body vessel.
Figure 18B:
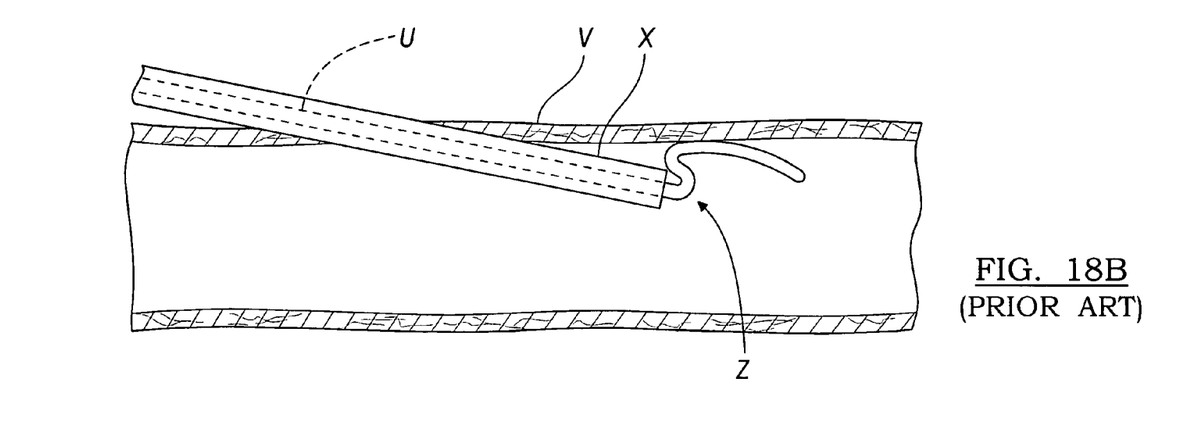
FIG. 18b is an environmental view of the wire guide shown in FIG. 18a having a catheter being advanced there along.

Wire guides (also known as guide wires) have been used in percutaneous entry procedures for diagnostic X-Ray studies and interventional procedures since about the 1950's when the idea of percutaneous, wire guided entry into the vasculature was conceived. As shown in FIGS. 18a and 18b, a wire guide U known in the prior art is typically inserted percutaneously into a body vessel V and advanced or manipulated within the body vessel V until reaching a desired location W. A catheter X (or other insertable device) is then positioned over the wire guide U, inserted percutaneously into the body vessel V, and advanced along the wire guide U to a desired location to perform a desired treatment, diagnosis, investigation, or medical intervention.

Therefore, wire guides typically have particular characteristics to improve the pushability of the wire guide U within the body vessel V. For example, the wire guide U is preferably generally radially flexible to negotiate the potentially-winding path of the body vessel V and to reduce potential damage to the body vessel walls while the wire guide U is being advanced. More specifically, wire guides U typically include a distal tip Y that is generally radially flexible. As another example, the wire guide shaft Z preferably has a relatively high axial stiffness to improve the pushability and control of the wire guide U along the body vessel V. The relatively high axial stiffness reduces kinking and bending so that the wire guide U will not become stuck or obstructed during the advancement thereof along the body vessel V. The axial stiffness of the wire guide shaft Z is preferably sufficient to prevent the wire guide U from folding over itself and becoming obstructed within the body vessel V when the distal tip Y encounters a bend in the body vessel V.

However, after being positioned as desired in the body vessel V, currently known wire guides may become tangled or obstructed during the advancement of the catheter X over the wire guide U. For example, the advancing catheter X may encounter a slightly curved portion of the wire guide U and undesirably exaggerate the curve of the wire guide U. More specifically, the curved wire portion may bend around the rim of the catheter X and bend the wire guide U into S-shaped curve Z, thereby resisting or preventing advancement of the catheter X.

It may be undesirable or difficult to improve the advanceability of the catheter along the wire guide by increasing the diameter or the axial stiffness of the wire guide because such a design change may decrease the pushability of the wire guide within the body vessel. For example, a wire guide with increased axial stiffness may not have enough radial flexibility to negotiate the winding path of the body vessel or may damage the body vessel while doing so. As another example, an increased-diameter wire guide may not be small enough to be received by the catheter or may be undesirably invasive to the body vessel.

Another disadvantage to the current design is that it may be difficult for the physician to keep the distal end of the wire guide properly positioned at the target site. For example, once the physician positions the wire guide at the desired location, the wire guide may migrate to another position within the body vessel. More specifically, the advancing catheter may bend the wire guide and cause the distal end of the wire guide to move from its desired position, as discussed above.

It is therefore desirous to provide a wire guide with a relatively small diameter that is able to be effectively pushed into a desired position, that is able to be received by a catheter, that is able to permit advancement of a catheter there along, and that is able to maintain its position at a desired location.

SUMMARY

In overcoming the limitations and drawbacks of the prior art, one aspect of the present invention provides a wire guide for percutaneous guidance within a body vessel. The wire guide includes an outer component for insertion into the body vessel and a core wire disposed in the outer component and movable between first and second positions. The core wire includes an engaging portion that extends from the outer component to engage the body vessel when the core wire is in the second position.

In one aspect of the invention, the engaging portion is an anchoring portion for extending into a wall of the body vessel and anchoring the wire guide thereto when the core wire is in the second position. The engaging portion may also be a drug delivery portion for delivering a drug to the body vessel. The drug delivery portion may be located at a distal tip of the core wire, or it may be proximal of the distal tip.

In another aspect of the present invention, the outer component is a coiled wire. More particularly, the outer component may be defined by a multiple filament, helically wound row of wires. When in the second position, the core wire extends between adjacent coils of the coiled wire. Alternatively, the core wire extends from a distal tip of the outer component when in the second position.

The engaging portion may be a tapered tine, a spiral-shaped portion, a barb portion, or any other suitable shaped portion. The core wire may also include a second engaging portion extending from the outer component when the core wire is in the second position. The engaging portion may be completely within the outer component when the core wire is in the first position.

In yet another aspect of the present invention, a wire guide is provided for guidance within a body vessel, the wire guide including a distal portion, a proximal portion, and a body portion. The distal portion includes an end portion for insertion into a wall of the body vessel and a stop portion having an effective diameter substantially greater than that of the end portion so as to resist insertion of the end portion into the wall beyond a maximum insertion distance.

In one design, the stop portion is a protrusion extending from the distal portion of the wire guide in a direction generally perpendicular a longitudinal axis of the wire guide. The stop portion is preferably more flexible when urged towards the distal end than when urged towards the proximal end. In another design, the stop portion is a loop portion having first and second ends attached to the wire guide.

During the initial percutaneous delivery of the wire guide to the body vessel, a sheath may be disposed over the distal portion to radially constrain the stop portion and facilitate delivery of the wire guide.

In another aspect of the present invention, a method of engaging a wire guide with a body vessel is provided, including the steps of: inserting the wire guide into the body vessel, extending an engaging portion of the wire guide into an engaging position, and engaging the body vessel with the engaging portion to anchor the wire guide thereto.

The method may also include the step of applying a desired force to the wire guide in a direction extending away from the body vessel. The method may also include the step of advancing a catheter along the wire guide and into the body vessel.

In yet another aspect of the present invention, an assembly for insertion within a body vessel is provided, including a wire guide and a catheter having a receiving portion configured to receive the wire guide and to be advanced there along into the body vessel.

The present invention may be used in a blood vessel for various procedures, such as the treatment of stenotic lesions. Alternatively, the present invention may be used in a nonvascular system, such as the urinary tract or the biliary system, for the advancement of medical instruments, such as a laparoscope.

Further objects, features and advantages of this invention will become readily apparent to persons skilled in the art after a review of the following description, with reference to the drawings and claims that are appended to and form a part of this specification.

DETAILED DESCRIPTION

Figure 1:
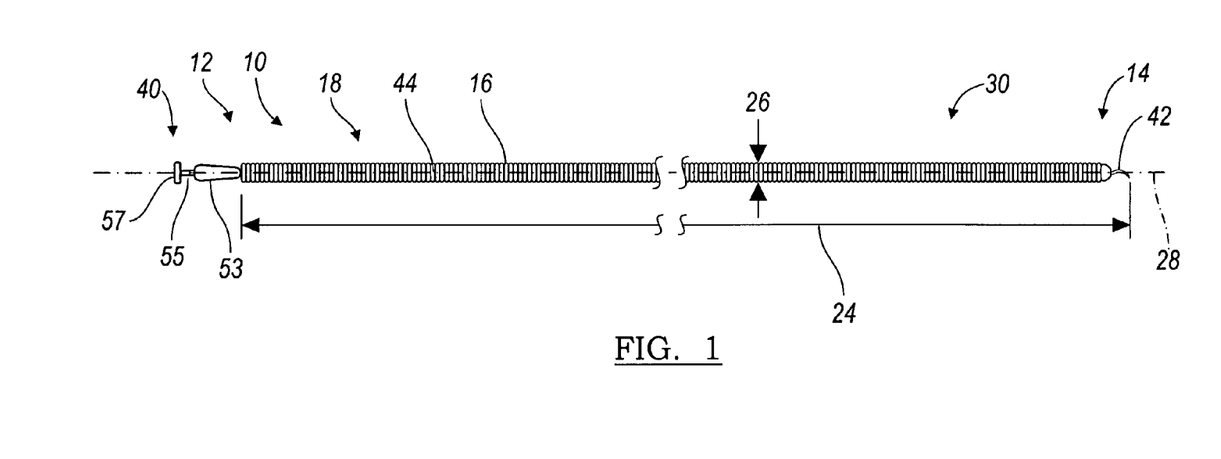
FIG. 1 is a side view of a wire guide embodying the principles of the present invention and being used for percutaneous guidance within a body vessel.

Referring now to the drawings, FIG. 1 shows a wire guide 10 for percutaneous insertion within a body vessel. The wire guide 10 includes a proximal end 12 for controlling and advancing the wire guide 10, a distal end 14 for engaging and disengaging inner surfaces of the body vessel, and a body portion 16 extending between the proximal and distal ends 12, 14. The body portion 16 and the distal end 14 cooperate to define an effective length 24, which is generally defined as the length of the wire guide 10 that is able to be inserted into the body vessel. The distal end 14 is preferably generally tapered and the body portion 16 has a generally constant diameter 26 to improve the ease of insertion into the body vessel. Despite being generally radially flexible, the wire guide 10 extends generally linearly along a longitudinal axis 28 when in a relaxed state 30.

Figure 2A:
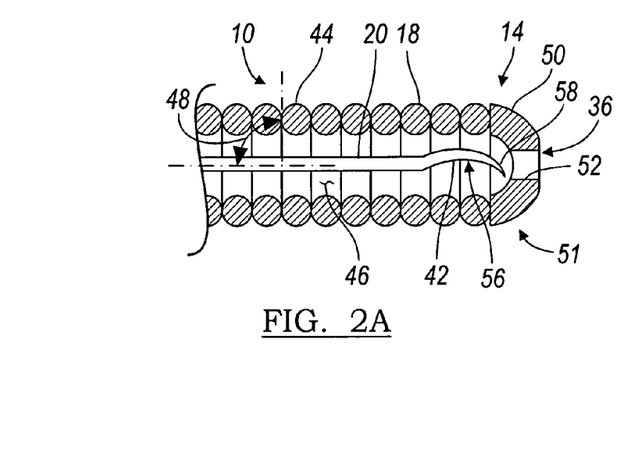
FIG. 2a is an enlarged cross-sectional view of the wire guide shown in FIG. 1, where the core wire of the wire guide is in a retracted position.

As shown in FIGS. 1 and 2a, the wire guide 10 generally includes: an outer component 18 defining the outer surface of the wire guide 10; a core wire 20 moveably received within the outer component 18 between a retracted position 36 and an extended position 38; and an actuator 40 for controlling the movement of the core wire 20. The core wire 20 includes an engaging portion that selectively engages a wall of the body vessel when the core wire 20 is in the extended position 38. For example, in FIGS. 2a and 2b, the engaging portion is an anchoring portion 42 configured to extend into the body vessel wall and anchor the wire guide 10 thereto.

The outer component 18, preferably defined by a coiled wire 44, defines a conduit 46 for receiving the core wire 20. For example, the coiled wire 44 is a tightly wound helical coil having an axial stiffness and a radial flexibility that are conducive to navigation of tortuous pathways of the body vessel. The wire guide 10 preferably increases in radial stiffness from the distal end 14 towards the proximal end 12. Additionally, the wire guide 10 may be made of any suitable material or combination of materials that are biocompatible or capable of being made biocompatible, such as stainless steel, other biologically compatible metals, polymers, plastics, alloys (including super-elastic alloys), or composite materials. In one example, the distal end 14 and the body portion 16 intermediate section 44 comprise a nickel-titanium alloy (commonly known as "nitinol," an acronym of Nickel Titanium Naval Ordnance Laboratory, where the alloy's properties were discovered). Nitinol is an alloy containing nearly equal numbers of nickel and titanium atoms, and the relative amounts of nickel and titanium can be varied by a few percent.

The outer component 18 shown in FIG. 2a has a single coiled wire wound at a pitch angle 48 suitable for a desired flexibility. A relatively steep pitch angle 48, where a steep pitch angle 48 is defined as being generally close to 90 degrees, is typically more flexible than a generally shallow pitch angle. The pitch angle 48 of the coiled wire 44 may vary along the length of the wire guide 10 to affect the radial stiffness thereof. For example, the pitch angle 48 is typically steeper at the distal end 14 of the wire guide 10 where radial flexibility is generally desirable.

Figure 2B:
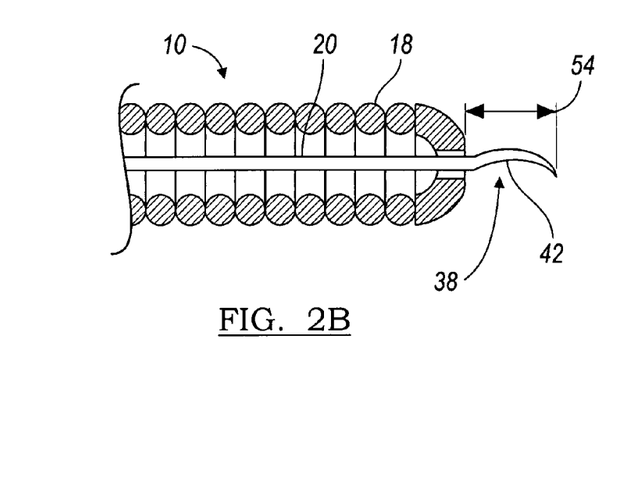
FIG. 2b is an enlarged cross-sectional view of the wire guide shown in FIG. 2a, with the core wire in an extended position.

An end cap 50 cooperates with the coiled wire 44 to define the conduit 46 and the distal end 14 of the wire guide 10 in FIGS. 2a and 2b. More specifically, the end cap 50 is located at a distal tip 51 of the wire guide 10 and defines an aperture 52 generally aligned with the wire guide longitudinal axis 28 so that the anchoring portion 42 extends through the aperture 52 when the core wire 20 is in the extended position 38. The diameter of the aperture 52 is preferably smaller than the inner diameter of the coiled wire 44 to provide a controlled delivery of the anchoring portion 42 from the end cap 50 while providing an increased radial flexibility of the body portion 16 of the wire guide 10. The end cap 50 may be connected to the coiled wire 44 by any suitable method, such as welding, or connecting the components via an adhesive or a fastener. Alternatively, the end cap and the coiled wire are a single, unitary component. For example, the end cap in this alternative design is the distal coil of the coiled wire. The end cap 50 may be made of a radiopaque material that is visible within a patient's body via a fluoroscope or a magnetic resonance (M.R.) machine, such as gold, tungsten or platinum materials, to allow the physician to track the progress of the wire guide 10 during the medical procedure.

The core wire 20, when in the retracted position 36, is preferably completely contained within the outer component 18 so as to avoid undesirable and/or premature engagement between the anchoring portion 42 and the body vessel. This configuration permits the anchoring portion 42 of the core wire 20 to be secured within the outer component 18 without the need for a sheath, thereby minimizing part complexity and reducing the outer diameter of the wire guide. As another benefit of this configuration, the anchoring portion 42 is able to be deployed into the extended position 38 without removing a component, such as a sheath, from the wire guide 10 and without changing the outer diameter of the wire guide.

The core wire 20, when in the extended position 38, preferably extends from the aperture 52 by an extension distance 54 that is between 0.1 and 20.0 millimeters. More preferably, however, the extension distance 54 is between 2.0 and 10.0 millimeters. However, any suitable extension distance 54 may be used with the present invention.

The extension distance 54 may have a predetermined maximum value by providing a core wire hard stop. For example, the actuator shown in FIG. 1 includes a base 53, a plunger shaft 55 slidably received by a passageway defined by the base 53, and a shoulder portion 57. The base 53 is coupled with the outer component 18 and the plunger shaft 55 is coupled with the core wire 20 such that the core wire 20 moves with respect to the outer component 18 when the plunger shaft 55 moves with respect to the base 53. Additionally, the shoulder portion 57 has a diameter that is greater than that of the passageway defined by the base 53 so that the plunger shaft 55 has a limited travel distance in the forward direction (as oriented from the left to the right in FIG. 1). The shoulder portion 57 also serves as a convenient and simple surface to be depressed by the physician. The base 53 and the shoulder portion 57 preferably have a diameter less than of equal to the outer diameter of the wire guide 10 so that the catheter 72 is able to be advanced over the wire guide 10.

In an alternative design from that shown in FIG. 1, the actuator base includes a pair of adjacent circular rings for receiving two of the physician's fingers and the actuator shoulder portion includes a single ring for receiving the physician's thumb. In another alternative design, the position of the core wire 20 is controlled by a removable device having an actuating mechanism, not unlike a syringe.

Alternatively, the physician may have broad control over the extension distance 54 by feeding a desired length of the core wire 20 through the outer component 18. When determining the extension distance 54, several factors may be considered, such as the thickness of the body vessel walls, the position of the anchoring portion 42 with respect to the outer component 18, the angle at which the anchoring portion 42 extends from the outer component 18, and the shape of the anchoring portion 42. In one example, if the physician desires to insert the tip of the anchoring portion 42 within the body vessel wall without actually extending completely through the body vessel wall, the physician may consider the thickness of the body vessel wall, the angle at which the anchoring portion 42 extends from the outer component 18, and the shape of the anchoring portion 42 to determine the extension distance 54.

The anchoring portion 42 shown in FIGS. 2a and 2b is a tine 56 having a tapered portion 58 for piercing and/or becoming embedded within the body vessel wall. The tine 56 has a generally curved shape so as to curl towards the body vessel wall to improve the ease at which the wire guide 10 becomes anchored to the body vessel. The curved shape of the tine 56 also creates a more secure connection between the core wire 20 and the body vessel to prevent undesirable movement of the wire guide 10.

Figure 3:
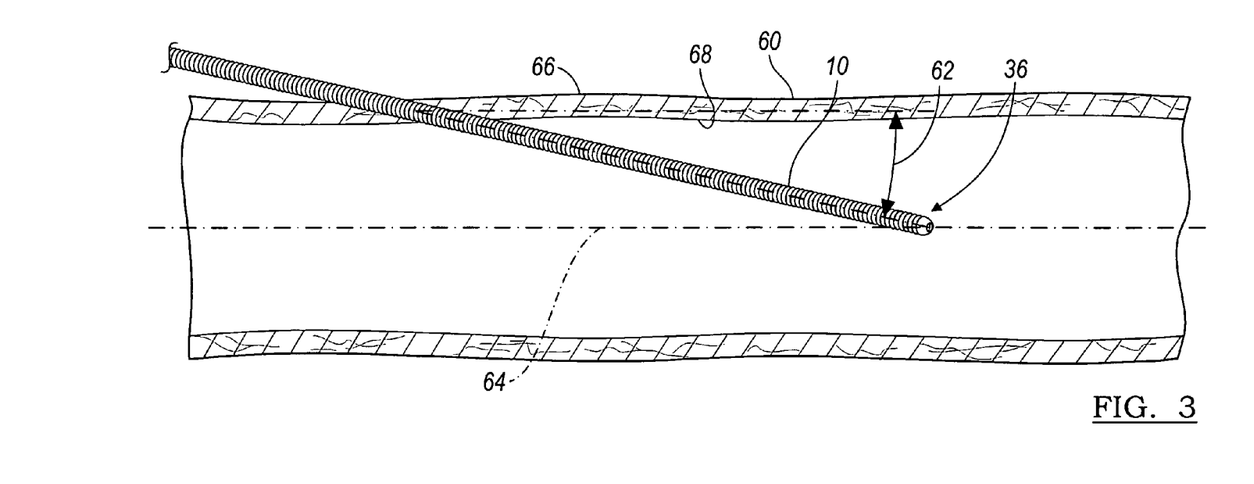
FIG. 3 is a environmental view of the wire guide from FIG. 1 being inserted into a body vessel, where the core wire is in the retracted position.

FIG. 3 shows the wire guide 10 being inserted into a body vessel 60 at an angle of entry 62 with respect to the body vessel longitudinal axis 64 during an initial stage of the wire guide delivery. During the initial stage, which includes piercing the wire guide 10 through a body vessel wall 66 and advancing the wire guide 10 along the body vessel 60 to the desired position, the core wire 20 is in the retracted position 36 to avoid snagging or becoming anchored to an inner wall 68 of the body vessel 60.

Figure 4:
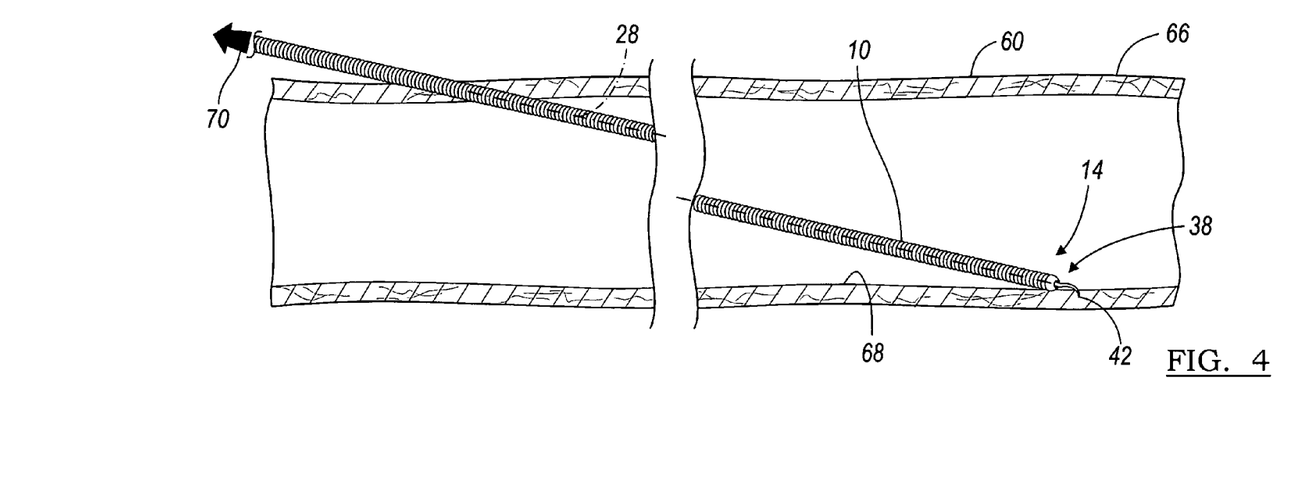
FIG. 4 is an environmental view of the wire guide from FIG. 3 engaging the body vessel, where the core wire is in the extended position.

Next, as shown in FIG. 4, the wire guide 10 is pushed along the body vessel 60 until reaching its desired location, where it engages the body vessel inner wall 68. For example, once the distal end 14 of the wire guide 10 contacts the body vessel inner wall 68, the core wire 20 is advanced into the extended position 38 to anchor itself to the body vessel 60. Alternatively, the core wire 20 is advanced shortly before the distal end 14 engages the body vessel 60, while the wire guide 10 is still being advanced forward. The anchoring portion 42 is shown in FIG. 4 as being partially embedded within the body vessel wall 66. More specifically, the anchoring portion 42 extends approximately half-way into the body vessel wall 66 to form a generally secure connection without extending through the body vessel wall 66.

Figure 5A:
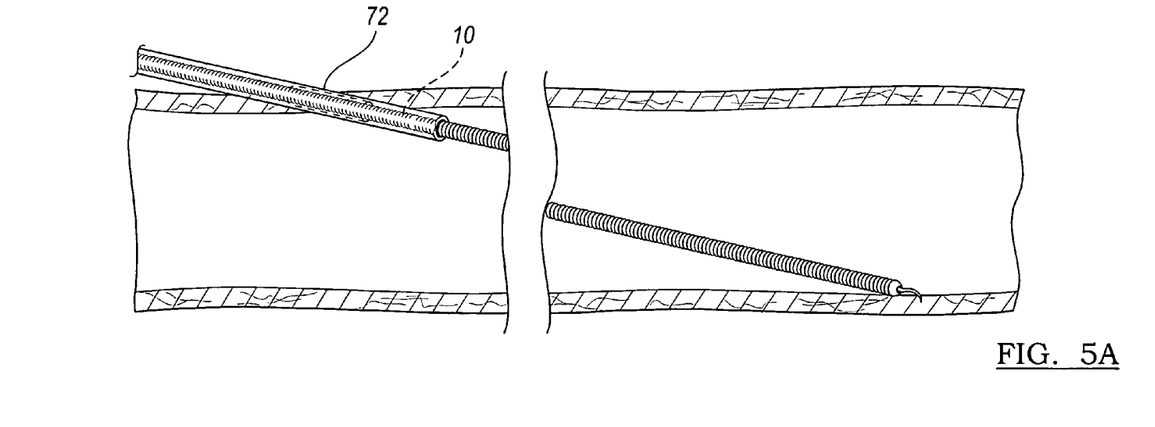
FIG. 5a is an environmental view of the wire guide from FIG. 4, where the core wire extends into the body vessel wall and the catheter is being advanced along the wire guide.

Once the wire guide 10 is anchored to the body vessel 60, a tensile force 70 is applied to the proximal end 12 of the wire guide 10 to improve the axial stiffness of the wire guide 10. For example, a slight force (generally less than 1 Newton) is applied along the wire guide 10 longitudinal axis 28 in a direction away from the body vessel 60 to cause the wire guide 10 to become generally taut. More specifically, a physician may pull the distal end 14 of the wire guide 10 away from the body vessel by pulling on the actuator base 53. The taut nature of the wire guide 10 reduces the bends of the body portion 16; thereby reducing the points along the wire guide 10 at which a catheter 72 (FIG. 5) is likely to become entangled with the wire guide 10. Additionally, the taut nature of the wire guide 10 increases the radial stiffness of the wire guide; thereby reducing the ease at which the catheter 72 may become entangled with the wire guide 10. The preferred magnitude of the force 70 depends on various factors, such as the type and the condition of the body vessel. For example, a body vessel in the patient's brain probably requires a smaller retraction force than a body vessel in the patient's leg.

Additionally, the taut wire guide 10 is able to provide improved travel by the catheter 72 through occluded or narrowed portions of the body vessel 60. For example, the taut wire guide 10 reduces or minimizes radial movement of the wire guide 10 and thereby reduces or minimizes radial movement of the catheter 72 while moving there along. This is especially beneficial while moving through occluded or narrowed portions of the body vessel 60 where a radial movement of the wire guide 10 may increase resistance to the forward movement of the catheter 72. Additionally, the taut state of the wire guide 10 provides counter-traction to the forward movement of the catheter 72 and reduces resistance thereto.

The anchoring portion 42 may be disengaged from the body vessel wall 66 by various methods, the implementation of which may depend on the shape of the anchoring portion 42. For example, the wire guide 10 is preferably disengaged from the body vessel 60 by simultaneously applying a slight force in the forward direction (opposite to the direction of the force 70 shown in FIG. 4) while pivoting the wire guide 10 about the entry point into the body vessel 60 to move the distal end 14 away from the body vessel wall 66. Alternatively, or in addition to, the catheter 72 may be advanced until contacting the body vessel wall 66 and pushing the body vessel wall 66 away from the core wire 20.

Figure 5B:
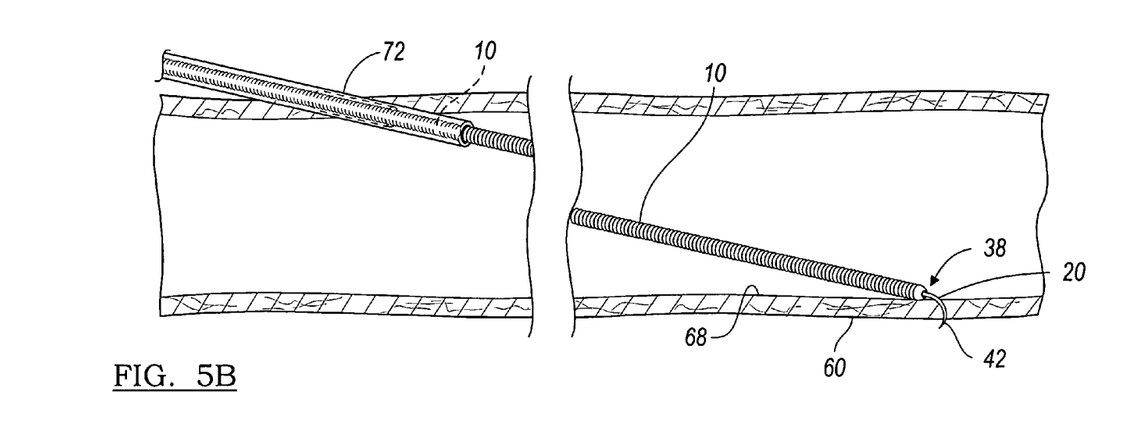
FIG. 5b is an environmental view of the wire guide from FIG. 4, where the core wire extends through the body vessel wall and the catheter is being advanced along the wire guide.

FIG. 5a shows the core wire in an extended position such as to extend into the wall of the body vessel wall so the catheter can be advanced along the wire guide. Additionally, FIG. 5b shows the core wire 20 in an extended position 38 further advanced than that shown in FIGS. 4 and 5a so as to pin the body vessel inner wall 68. More specifically, the core wire 20 extends through the body vessel 60 wall so as to form a potentially more secure engagement therewith than in the engagement shown in FIGS. 4 and 5a.

Figure 6A:
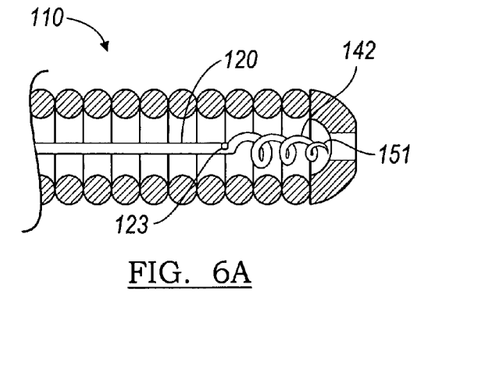
FIG. 6a is an enlarged cross-sectional view of a wire guide having an alternative design embodying the principles of the present invention, with the core wire in a retracted position.
Figure 6B:
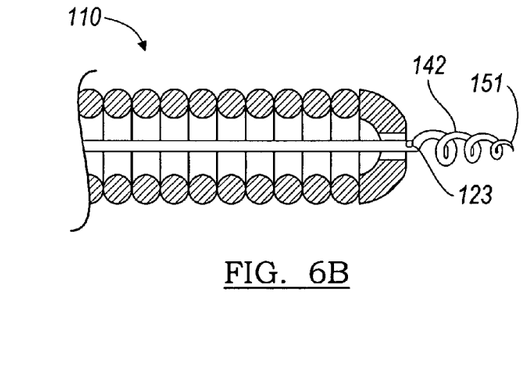
FIG. 6b is an enlarged cross-sectional view of the wire guide shown in FIG. 6a, with the core wire in an extended position.

FIGS. 6a and 6b show an alternative wire guide 110 having a spiral-shaped anchoring portion 142 that tapers as it spirals. The spiral-shaped anchoring portion 142 may be especially useful for slowly and precisely advancing the spiral-shaped anchoring portion 142 into the body vessel wall 66. For example, the spiral-shaped anchoring portion 142 may be rotated by the physician, thereby causing the spiral-shaped anchoring portion 142 to screw itself into the body vessel wall 66. A reverse-direction rotation can be used to remove the spiral-shaped anchoring portion 142 from the body vessel wall 66.

Figure 7A:
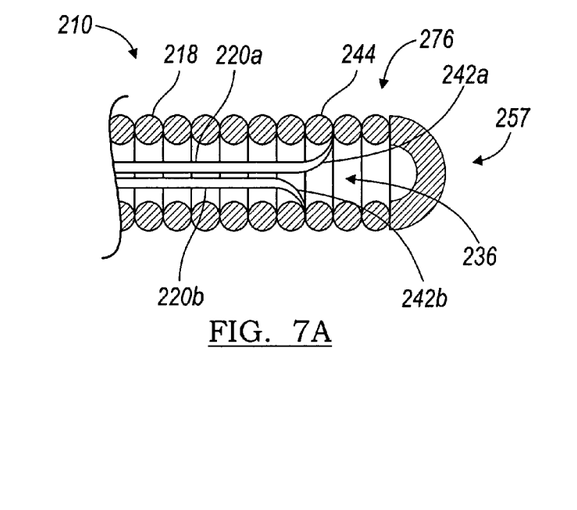
FIG. 7a is an enlarged cross-sectional view of a wire guide having another alternative design embodying the principles of the present invention, with the core wire in a retracted position.
Figure 7B:
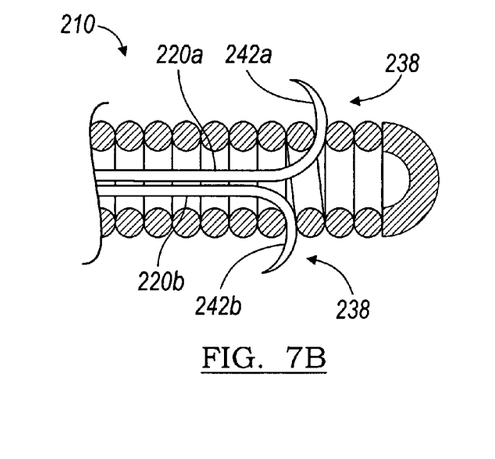
FIG. 7b is an enlarged cross-sectional view of the wire guide shown in FIG. 7a, with the core wire in an extended position.

FIGS. 7a and 7b show another alternative wire guide 210, where the core wire includes a pair of core wire portions 220a, 220b, each having an anchoring portion 242a, 242b that is able to move between a retracted position 236 and an extended position 238. Each of the anchoring portions 242a, 242b is positioned adjacent to, or in contact with, an engagement point between adjacent coils of the coiled wire 244, so that the anchoring portions 242a, 242b extend between the adjacent coils upon the advancement of the core wire portions 220a, 220b. The anchoring portions 242a, 242b extend from side portions 276 of the outer component 218, rather than the distal tip 251, which may improve the ease at which the wire guide 210 is anchored to the body vessel wall. Also, the plurality of anchoring portions 242a, 242b allows more opportunities for the wire guide 210 to be anchored to the body vessel. Additionally, the anchoring portions 242a, 242b preferably are slightly curved back toward the proximal end of the wire guide 210 so as to more securely anchor within the body vessel wall. The anchoring portions 242a, 242b are preferably disengaged from the body vessel wall by pushing forward on the actuator base and pulling back on the actuator shoulder, thereby retracting the respective portions 242a, 242b into the retracted position 236.

Figure 8A:
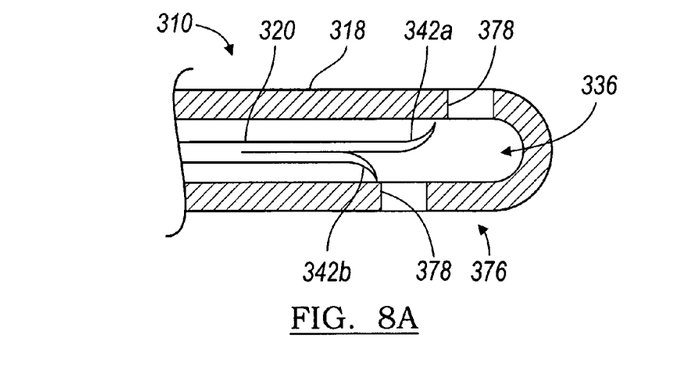
FIG. 8a is an enlarged cross-sectional view of a wire guide having yet another alternative design embodying the principles of the present invention, with the core wire in a retracted position.
Figure 8B:
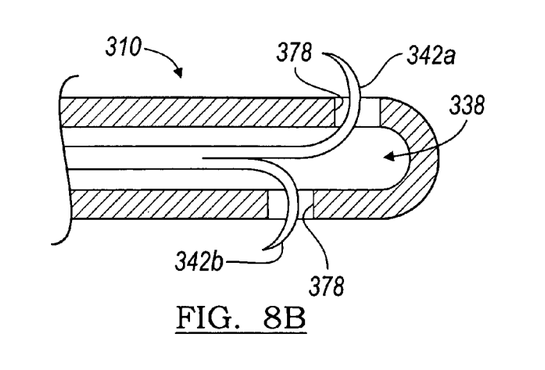
FIG. 8b is an enlarged cross-sectional view of the wire guide shown in FIG. 8a, with the core wire in an extended position.

FIGS. 8a and 8b show yet another alternative wire guide 310, where the core wire 320 splits into a pair of anchoring portions 342a, 342b that are each able to move between a retracted position 336 and an extended position 338. Each of the anchoring portions 342a, 342b is positioned adjacent to an opening 378 defined by the outer component 318 so that the anchoring portions 342a, 342b extend through the respective openings 378 upon the advancement of the core wire 320. The anchoring portions 342a, 342b are biased to have a spring-type force urging radially outwardly so as to extend substantially radially outwardly once they enter the openings 378. To provide a smooth, low friction contact between the anchoring portions 342a, 342b and the outer component inner surface, the outer component 318 is preferably a solid sleeve rather than a coiled wire as described above. The anchoring portions 342a, 342b extend from side portions 376 of the outer component 318. Additionally, the anchoring portions 342a, 342b preferably are slightly curved back toward the proximal end of the wire guide 310 so as to more securely anchor within the body vessel wall. The anchoring portions 342a, 342b are preferably disengaged from the body vessel wall by pushing forward on the actuator base and pulling back on the actuator shoulder, thereby retracting the respective portions 342a, 342b into the retracted position 336.

Figure 9A:
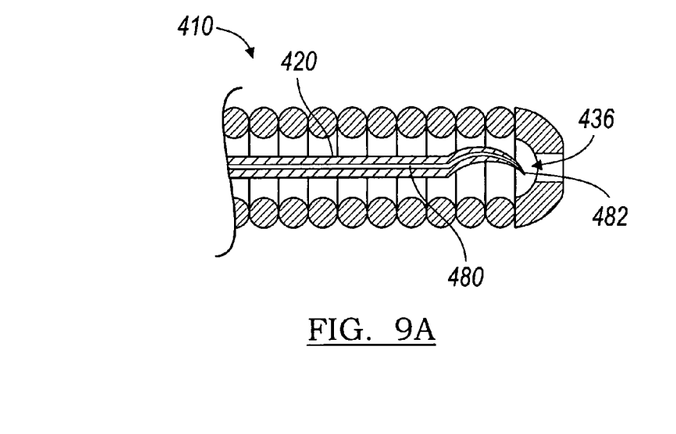
FIG. 9a is an enlarged cross-sectional view of a wire guide having yet another alternative design embodying the principles of the present invention, with the core wire in a retracted position.
Figure 9B:
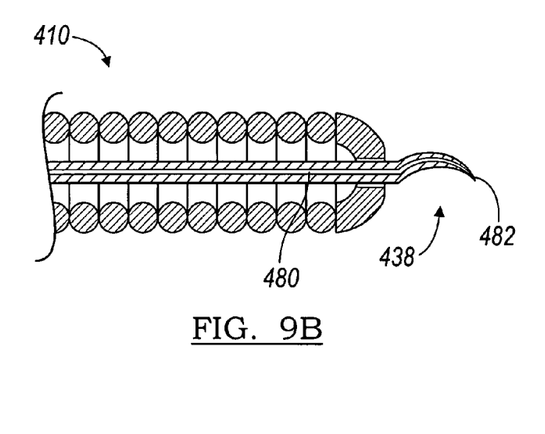
FIG. 9b is an enlarged cross-sectional view of the wire guide shown in FIG. 9a, with the core wire in an extended position.

FIGS. 9a and 9b show another alternative wire guide 410, where the core wire 420 is a hollow tube used for the delivery of a drug into the body vessel. For example, the core wire 420 defines a passageway 480 for storing a drug and for delivering the drug to a localized portion of the body vessel. The passageway 480 has an open distal tip 482 so that the drug can be actively injected along the passageway 480 and through the open distal tip 482 or so that the drug naturally flows into or becomes absorbed by the body vessel. The drug delivery into the body vessel is advantageous over currently known methods because the drug is more locally-delivered and locally-concentrated than a general injection into the blood stream of the body vessel. The core wire 420 may also, or alternatively, be used to scrape or cut a targeted section of the body vessel. This may be accomplished by moving the actuator shoulder with respect to the base, or by moving the entire wire guide 410 with respect to the body vessel. Additionally, the core wire 420 has a generally curved portion 284 similar to that shown in FIGS. 2a and 2b so that the wire guide 410 can be anchored to the body vessel in addition to the drug delivery function.

In one exemplary application, lytic agents are delivered to relatively small body vessels, such as blood vessels in the brain. In another exemplary application, chemotherapy agents are delivered to a body vessel. In yet another exemplary application, stem cells are delivered to a desired portion of a body vessel during a gene therapy procedure. The above applications, and other applications of the present invention as a drug delivery device, may be particular advantageous for targeting anatomic locations beyond the reach of standard catheters.

Referring back to FIGS. 6a and 6b, the wire guide 110 includes a drug delivery port 123 defined by a surface of the core wire 120 for delivering drugs to the body vessel. For example, the core wire 120 is a generally hollow tube defining a drug carrying-conduit for carrying a drug between a proximal portion of the wire guide 110 and the drug delivery port 123. In FIGS. 6a and 6b the drug delivery port 123 is proximal of the distal tip 151 so that the drug delivery port 123 is positioned within the bloodstream of the body vessel even when the anchoring portion 142 of the wire guide 110 is buried within the wall of the body vessel.

Figures 10A, 11A:
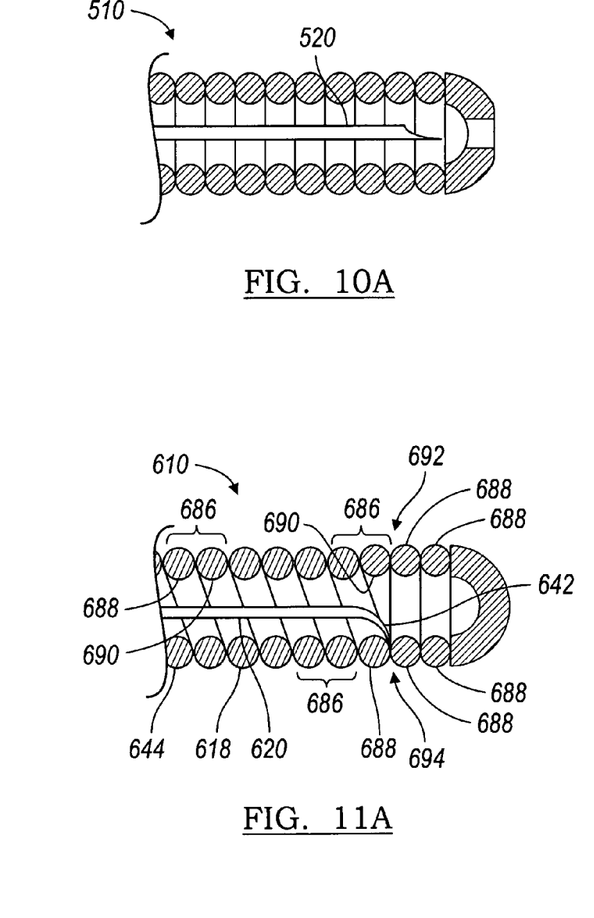
FIG. 10a is an enlarged cross-sectional view of a wire guide having another alternative design embodying the principles of the present invention, with the core wire in a retracted position.
FIG. 11a is an enlarged cross-sectional view of a wire guide having yet another alternative design embodying the principles of the present invention, with the core wire in a retracted position.
Figure 10B:
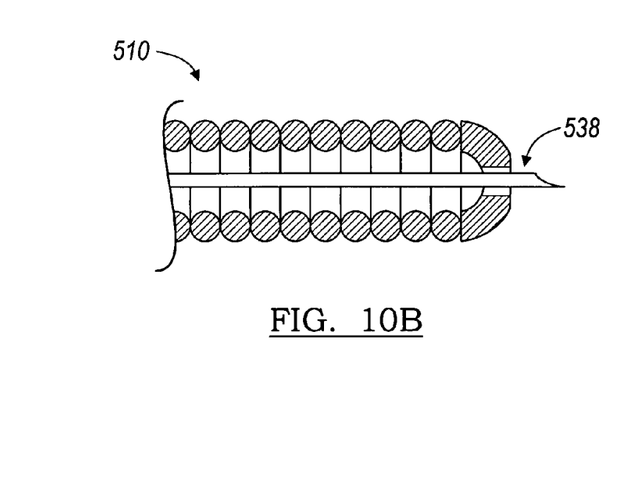
FIG. 10b is an enlarged cross-sectional view of the wire guide shown in FIG. 10a, with the core wire in an extended position.

FIGS. 10a and 10b show a wire guide 510 with a similar design to that in FIGS. 9a and 9b, but with a generally linear, hollow core wire 520 that extends linearly from the outer component 518 to deliver a drug to the body vessel when in the extended position 538. This wire guide 510 is used primarily for drug delivery, rather than for anchoring the wire guide 510 to the body vessel.

Figure 11B:
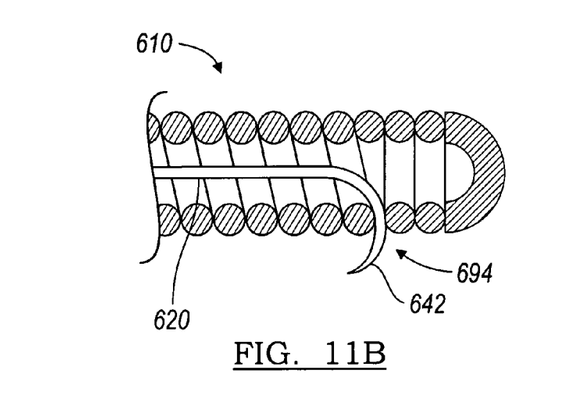
FIG. 11b is an enlarged cross-sectional view of the wire guide shown in FIG. 11a, with the core wire in an extended position.

FIGS. 11a and 11b show yet another alternative wire guide 610, where the anchoring portion 642 of the core wire 620 is positioned adjacent to, or in contact with, an engagement point between adjacent coils of the coiled wire 644, so that the anchoring portion 642 extends between the adjacent coils upon the advancement of the core wire 620, similar to the design shown in FIGS. 7a and 7b. However, in this design, the coiled wire 644 is defined by a multiple filament, helically wound row of wires 686, similar to that disclosed in the U.S. patent application entitled "ENDOVASCULAR MEDICAL DEVICE WITH PLURALITY OF WIRES" having Ser. No. 10/615,314, which was filed on Jul. 7, 2003 and which is incorporated herein by reference. For example, the helically wound row of wires 686 includes a first wire 688 and a second wire 690 that are wound adjacent to each other in a helical pattern. The pair of wires 688, 690 improve the rotatability and the radial stiffness of the wire guide 610, as well as preventing the core wire 620 from exiting the outer component 618 in an undesirable position, such as between the wrong pair of coils. For example, the outer component 618 in FIGS. 11a and 11b has a discontinuation point 692 where the second wire 690 is terminated and a small gap 694 is present between the coils of the first wire 688. Therefore, the core wire 620 tends to exit the outer component 618 at the gap 694, thereby increasing the predictability of the location of the anchoring point.

In yet another aspect of the present invention, a wire guide having a distal portion, a proximal portion, and a body portion is provided for guidance within a body vessel. The distal portion includes an end portion for insertion into a wall of the body vessel and a stop portion having a diameter substantially greater than that of the end portion so as to resist insertion of the end portion into the wall beyond a maximum insertion distance.

Figures 12, 13:
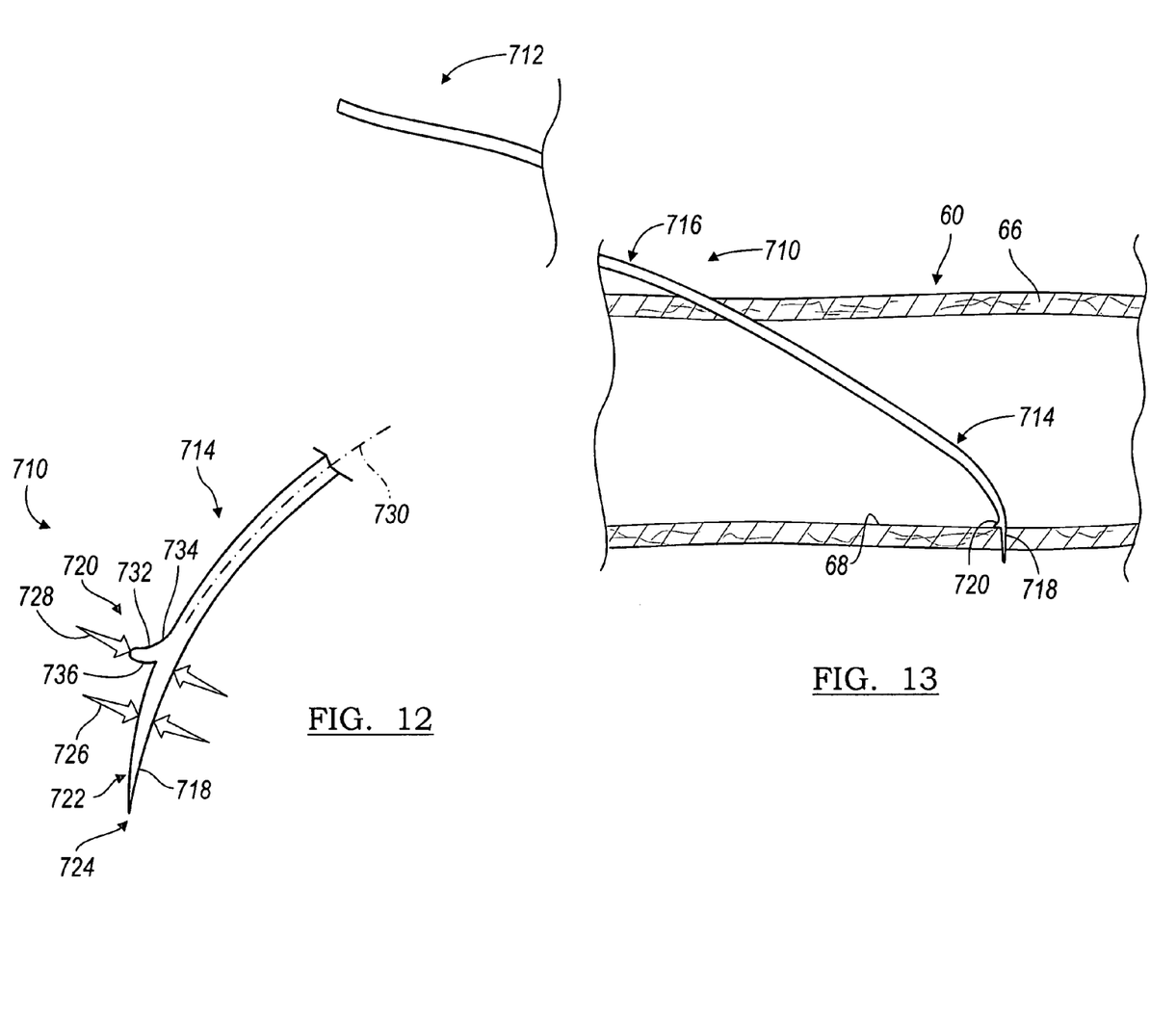
FIG. 12 is a side view of a distal portion of a wire guide having another alternative design embodying the principles of the present invention, where a stop portion prevents over-insertion of the wire guide into a body vessel wall.
FIG. 13 is an environmental view of the wire guide shown in FIG. 12 being inserted into a body vessel wall.
Figure 14:
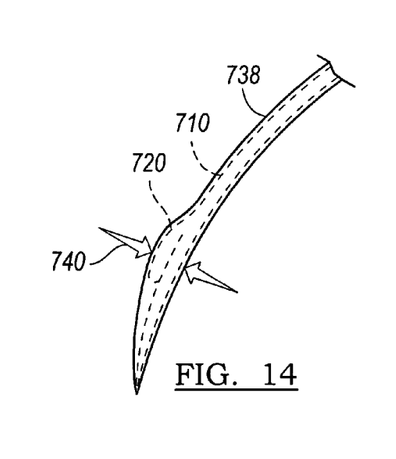
FIG. 14 is a side view the wire guide shown in FIG. 12 with a sheath disposed over the distal portion to radially constrain the stop portion.

FIGS. 12-14 show another alternative wire guide 710 generally including a proximal portion 712, a distal portion 714, and a body portion 716 extending between the proximal and distal portions 712, 714. The distal portion 714 includes an end portion 718 for insertion into a body vessel wall and a stop portion 720 for limiting the distance that the distal portion 714 is able to be inserted into the body vessel wall.

The end portion 718 is sized and shaped so as to facilitate insertion into the body vessel wall. For example, the end portion 718 shown in FIGS. 12-14 defines a generally tapered shape 722 and has a relatively sharp end tip 724. More specifically, the end portion 718 has a diameter 726 that gradually increases from the end tip 724 towards the proximal end 712.

The stop portion 720 defines an effective diameter 728 that is substantially greater than the diameter 726 of the end portion so as to prevent over-insertion of the wire guide 710 into the body vessel wall. For example, the stop portion 720 in FIGS. 12-14 is a protrusion 732 extending generally perpendicularly to a longitudinal axis 730 of the wire guide 710. The effective diameter 728 of the stop portion 720 and the diameter 726 of the end portion 718 are body measured along planes that are generally perpendicular to the longitudinal axis 730 of the wire guide 710. In other words, the diameters 726, 728 measure the cross-sectional of the wire guide 710 taken along a plane that is perpendicular to the longitudinal axis 730.

The protrusion 732 is configured to resist being bent or folded backwards towards the proximal end 712 of the wire guide so as to resist being advanced into a blood vessel wall. However, the protrusion is also configured to permit being bent or folded forwards towards the distal end 714 of the wire guide 710 so that the wire guide can be withdrawn from the blood vessel. More specifically, the proximal side 734 of the protrusion 732 defines a ramp-shaped transition surface extending from the wire guide body and the distal side 736 of the protrusion defines a generally abrupt transition surface extending perpendicularly from the wire guide end portion.

Referring now to FIG. 13, the wire guide 710 is shown disposed within a body vessel 60 and engaged with the body vessel wall 66. More specifically, the body portion 716 of the wire guide 710 has been inserted percutaneously within the body vessel 60 and the end portion 718 has been inserted into the body vessel wall 66 so that the stop portion 720 abuts against the body vessel inner wall 68.

FIG. 14 shows a sheath 738 disposed over the wire guide 710 to radially constrain the stop portion 720 and facilitate delivery of the wire guide 710 within the body vessel 60. More specifically, the sheath 738 is a flexible sleeve that is selectively disposed on the wire guide 710 to apply a radial compressive force to the stop portion 720 while the wire guide 710 is being delivered within the body vessel 60. As a result of the radial compressive force, the stop portion 720 is bent forward against the end portion 718 to minimize the diameter 740 of the stop portion 720. Then, once the distal portion has been delivered within the body vessel 60, the sheath 738 is removed from the wire guide 710 over the proximal portion 712 thereof and the stop portion 720 returns to its natural position as shown in FIG. 12.

Figures 15, 17:
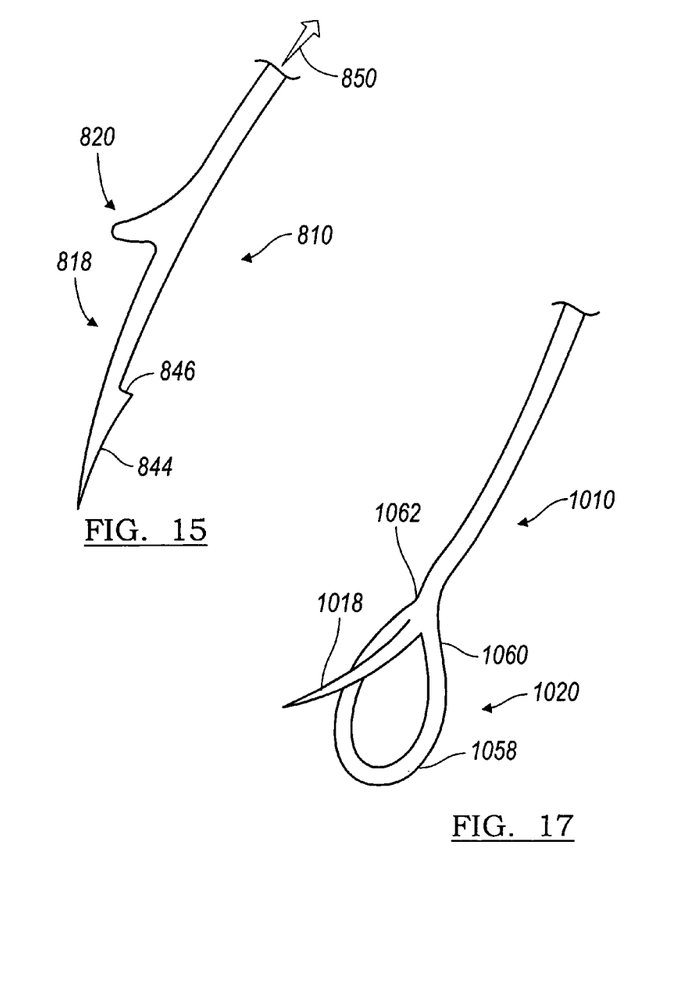
FIG. 15 is a side view of a distal portion of a wire guide having another alternative design embodying the principles of the present invention.
FIG. 17 is a side view of a distal portion of a wire guide having another alternative design embodying the principles of the present invention, where the stop portion includes a loop portion.

FIG. 15 shows another alternative wire guide 810 having an end portion 818 for insertion into the wall of a body vessel and a stop portion 820 for preventing over-insertion of the wire guide 810. Additionally, the end portion 818 includes an anchoring portion 844 for resisting removal of the end portion 818 from the body vessel wall. For example, the anchoring portion 844 shown in FIG. 15 is a barbed portion having a shoulder surface 846 for engaging an outer surface of the body vessel wall and resisting retraction of the wire guide 810 in the direction generally indicated by reference 850. Therefore, the stop portion 820 and the anchoring portion 844 cooperate to secure the wire guide 810 with respect to the body vessel 60 in two directions and to prevent both over-insertion and premature retraction. The end portion 818 of the wire guide 810 can be removed from the body vessel wall by pulling on the proximal end of the wire guide 810 with a sufficient force. Additionally, or alternatively, a sheath may be disposed over the wire guide 810 during delivery and/or removal of the wire guide 810 from the body vessel.

Figure 16:
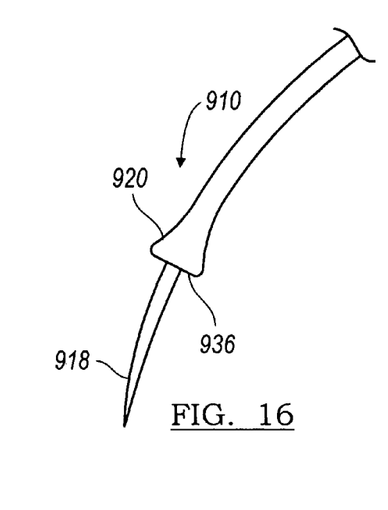
FIG. 16 is a side view of a distal portion of a wire guide having another alternative design embodying the principles of the present invention.

FIG. 16 shows another alternative wire guide 910 having an end portion 918 for insertion into the wall of a body vessel and a stop portion 920 for preventing over-insertion of the wire guide 910. The end portion 918 has a generally circular cross-section so that the end portion 918 extends along the central axis of the stop portion 918. As with the designs shown in FIGS. 12 and 15, the stop portion 920 has distal side 936 defining a generally abrupt transition surface extending perpendicularly from the wire guide end portion 918.

FIG. 17 shows yet another alternative wire guide 1010 having an end portion 1018 for insertion into the wall of a body vessel and a stop portion 1020 for preventing over-insertion of the wire guide 1010. The stop portion 1020 is a closed loop 1058 extending from the distal portion of the wire guide and having first and second ends 1060, 1062 attached thereto. More specifically, the ends 1060, 1062 extend from the distal portion of the wire guide towards the end tip of the end portion so that the loop expands when a force is applied to the loop from the distal end and compresses when a force is applied to the loop from the proximal end.

It is therefore intended that the foregoing detailed description be regarded as illustrative rather than limiting, and that it be understood that it is the following claims, including all equivalents, that are intended to define the spirit and scope of this invention.

What is claimed is:

1. A wire guide for percutaneous guidance within a body vessel, the wire guide comprising:
    an outer component percutaneously insertable in the body vessel, the outer component being at least partially defined by a coiled wire; and
    a core wire slidably disposed in the outer component and movable relative to the outer component between a first position and a second position, the core wire including an engaging portion that extends from a distal tip of the outer component to engage the body vessel when the core wire is in the second position, the distal tip of the outer component including an end cap defining an aperture configured to provide controlled delivery of the engaging portion from the end cap.

2. A wire guide as in claim 1, wherein the engaging portion is an anchoring portion configured to extend into a wall of the body vessel and anchor the wire guide thereto when the core wire is in the second position.

3. A wire guide as in claim 1, wherein the engaging portion is a drug delivery portion having a drug delivery conduit configured to deliver a drug to the body vessel when the core wire is in the second position.

4. A wire guide as in claim 1, wherein the outer component is defined by a multiple filament, helically wound row of wires.

5. A wire guide as in claim 1, wherein the engaging portion is a tine having a tapered portion configured to engage the body vessel.

6. A wire guide as in claim 1, wherein the engaging portion is generally spiral-shaped.

7. A wire guide as in claim 1, wherein the engaging portion includes a barb portion configured to engage the body vessel.

8. A wire guide as in claim 1, further comprising a second engaging portion, wherein the engaging portion and the second engaging portion extend from the distal tip of the outer component when the core wire is in the second position.

9. A wire guide as in claim 1, further comprising a stop portion extending from the core wire to resist insertion of the core wire into a wall of the body vessel beyond a maximum insertion distance.

10. An assembly for percutaneous insertion within a body vessel, the assembly comprising:
    a wire guide including an outer component being at least partially defined by a coiled wire having a first inner diameter and a core wire slidably disposed within the outer component, wherein the core wire is movable relative to the outer component between a first position and a second position and wherein the core wire includes an engaging portion that extends from a distal tip of the outer component to engage the body vessel when the core wire is in the second position, the distal tip of the wire guide including an end cap defining an aperture having a second diameter smaller than the first inner diameter of the coiled wire to provide a controlled delivery of the engaging portion from the end cap; and
    a catheter configured to receive the wire guide and to be advanced percutaneously within the body vessel.

* * * * *